350-96.26

XR 4,006,738

United States
Moore et al.

4,006,738
Feb. 8, 1977

[54] OTOSCOPE CONSTRUCTION

[75] Inventors: William C. Moore, Skaneateles; John D. Connors; Richard W. Newman, both of Auburn, all of N.Y.

[73] Assignee: Welch Allyn, Inc., Skaneateles Falls, N.Y.

[22] Filed: June 4, 1975

[21] Appl. No.: 583,748

[52] U.S. Cl. .................................. 128/9; 350/96 B
[51] Int. Cl.$^2$ ......................................... A61B 1/22
[58] Field of Search .................. 128/3, 6, 9, 11, 23, 128/13, 16, 18; 350/96 B

[56] References Cited
UNITED STATES PATENTS

| | | | |
|---|---|---|---|
| 1,635,822 | 7/1927 | DeZeng | 128/6 |
| 2,235,979 | 3/1941 | Brown | 128/6 |
| 3,592,199 | 7/1971 | Ostensen | 128/6 |
| 3,848,587 | 11/1974 | McDonald | 128/9 |

Primary Examiner—Robert W. Michell
Assistant Examiner—Henry S. Layton
Attorney, Agent, or Firm—Bruns & Jenney

[57] ABSTRACT

An improved construction for electrically illuminated otoscopes whereby more light is provided and the light is whiter and more uniform than the light output of prior art instruments. To obtain more light, a larger than normal lamp is employed which preferably is a halogen lamp as the latter gives a whiter light than a vacuum lamp and has a longer life span. Since a larger lamp produces more heat and would be more of an obstruction if positioned in the usual location, the lamp is positioned in the base of the instrument and its light is transmitted from there to a point in the viewing passage through the instrument by a bundle of optical fibers. The fiber bundle minimizes viewing passage obstruction and assists in providing the uniform, diffuse illumination that is desired without light loss.

9 Claims, 5 Drawing Figures

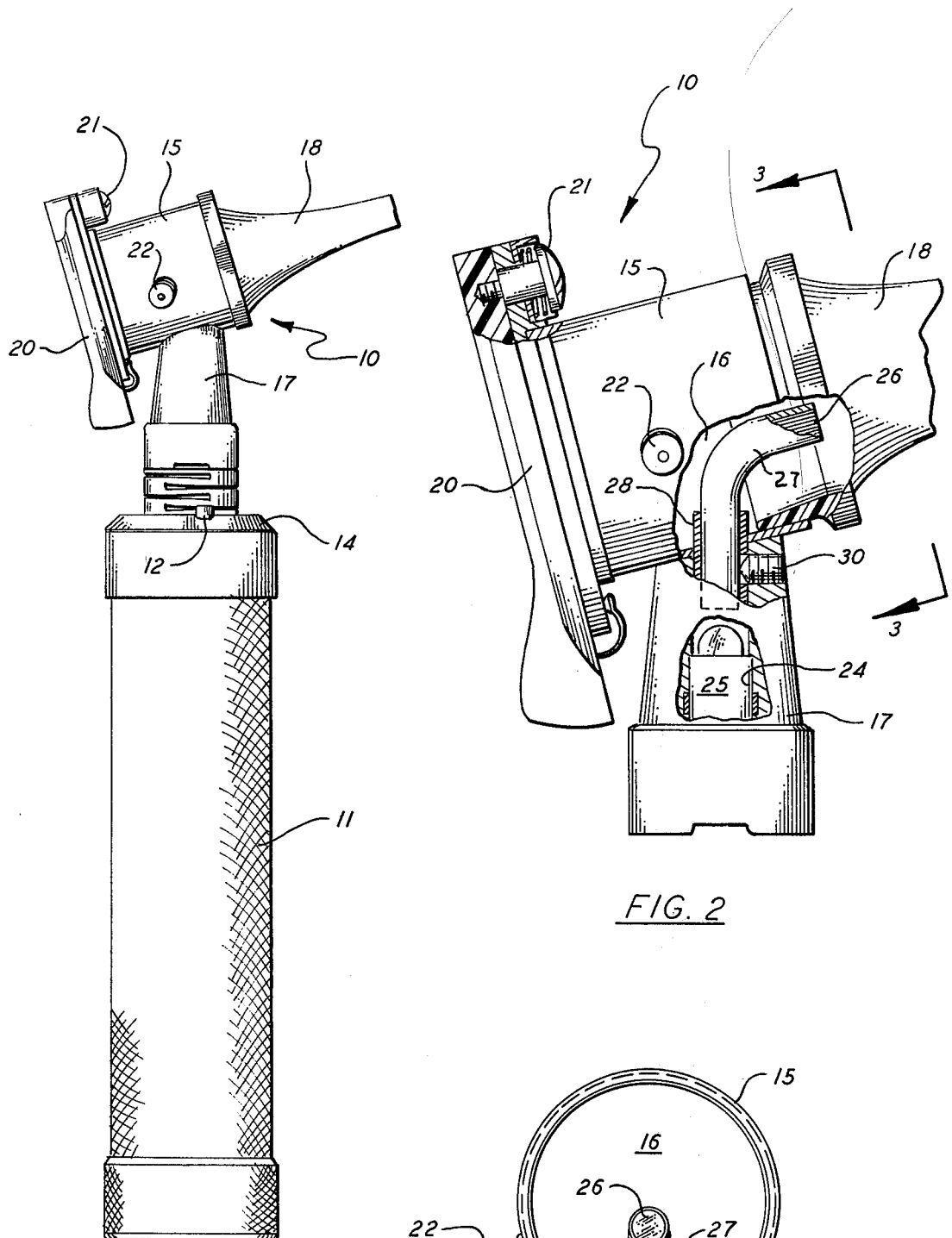
FIG. 1
FIG. 2
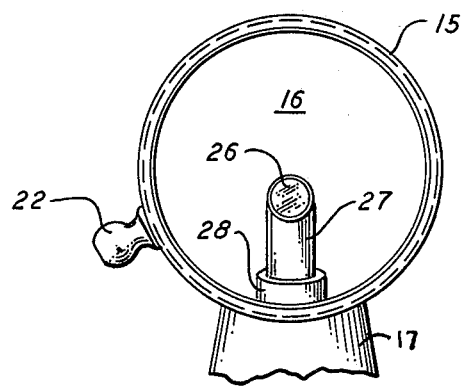
FIG. 3

OTOSCOPE CONSTRUCTION

BACKGROUND OF THE INVENTION

This invention relates generally to medical instruments, and has particular reference to an improved construction for electrically illuminated diagnostic instruments such as otoscopes.

In prior art otoscopes having their own light sources, problems with the quality of the illumination have always existed to a greater or lesser degree. Thus, in order to illuminate a field at the distal end of the viewing passage, it has been customary to position the lamp in the viewing passage as disclosed by U.S. Pat. Nos. 1,849,701 and 2,797,684 both owned by the assignee of the present invention. Unfortunately, with the lamp in this position, if it is large enough to provide as much illumination at the field of view as might be desired, it becomes an objectionable obstruction in the viewing passage. On the other hand, if a small lamp is employed to minimize the obstruction, there probably will be insufficient light at the field.

A solution to the problem just mentioned is to remove the lamp from the otoscope viewing passage altogether as disclosed in U.S. Pat. Nos. 3,373,737 and 3,698,387. These patents are also owned by the assignee of the present invention and represent the closest prior art known to the applicants. In the otoscope shown in each patent the lamp is located in the base of the instrument and optical fibers that are molded into the instrument head and speculum transmit the light from the lamp to the distal end of the speculum.

The fiber optic otoscopes just described have excellent performance for most applications and have been well received by the medical profession. There are, however, a number of physicians who still prefer the traditional, metal diagnostic and operating otoscopes as shown in U.S. Pat. Nos. 1,849,701 and 2,797,684, respectively. These instruments are more rugged than the molded plastic instruments and therefore are likely to have a longer, more trouble-free life. The metal otoscopes are at the same time less expensive than molded plastic instruments of the type shown in U.S. Pat. No. 3,698,387. Other reasons the traditional, metal otoscopes are preferred by some physicians are that their specula do not require added tip extensions, and they are well adapted for use with veterinary specula which the fiber optic otoscopes are not. It is an advantage also that the metal otoscopes can be used with their specula removed altogether which cannot be done with the fiber optic type and may be desirable under certain circumstances.

SUMMARY OF THE INVENTION

The present invention is directed toward improvements in the construction of metal diagnostic and operating types of otoscopes and has as its primary objective the provision of more light at the field of view while at the same time decreasing the size of the obstruction in the viewing passage. Other objects of the invention are to provide whiter light and more uniform, diffuse illumination. These objects are achieved without creating a heat problem such as would normally result from the use of a larger than normal lamp.

In accord with the invention, a larger than normal lamp is employed and this lamp is preferably a halogen lamp as the latter gives a whiter light than a vacuum lamp and has a substantially longer life. Because the lamp is relatively large, it is positioned in a recess in the base portion of the instrument and the surrounding metal functions as a heat sink for the heat that is generated. In addition, the recess provides a protected location for the lamp.

Light is transmitted from the lamp to a point in the viewing passage by a bundle of optical fibers encased in a metal tube. The tube diameter is less than that of a conventional lamp and therefore the tube is less of an obstruction. Because the light is transmitted by the fibers, there is no filament image on the illuminated field nor any unevenness in the light.

BRIEF DESCRIPTION OF THE DRAWINGS

FIG. 1 is a side elevation of a diagnostic type otoscope embodying the invention, the otoscope being mounted on a battery handle;

FIG. 2 is an enlarged, fragmentary side elevation of the otoscope of FIG. 1 with parts broken away to show the details of construction;

FIG. 3 is an enlarged, fragmentary front elevation of the otoscope with its speculum removed, the view being in the direction indicated by line 3—3 of FIG. 2;

DESCRIPTION OF THE PREFERRED EMBODIMENTS

Figure 4:
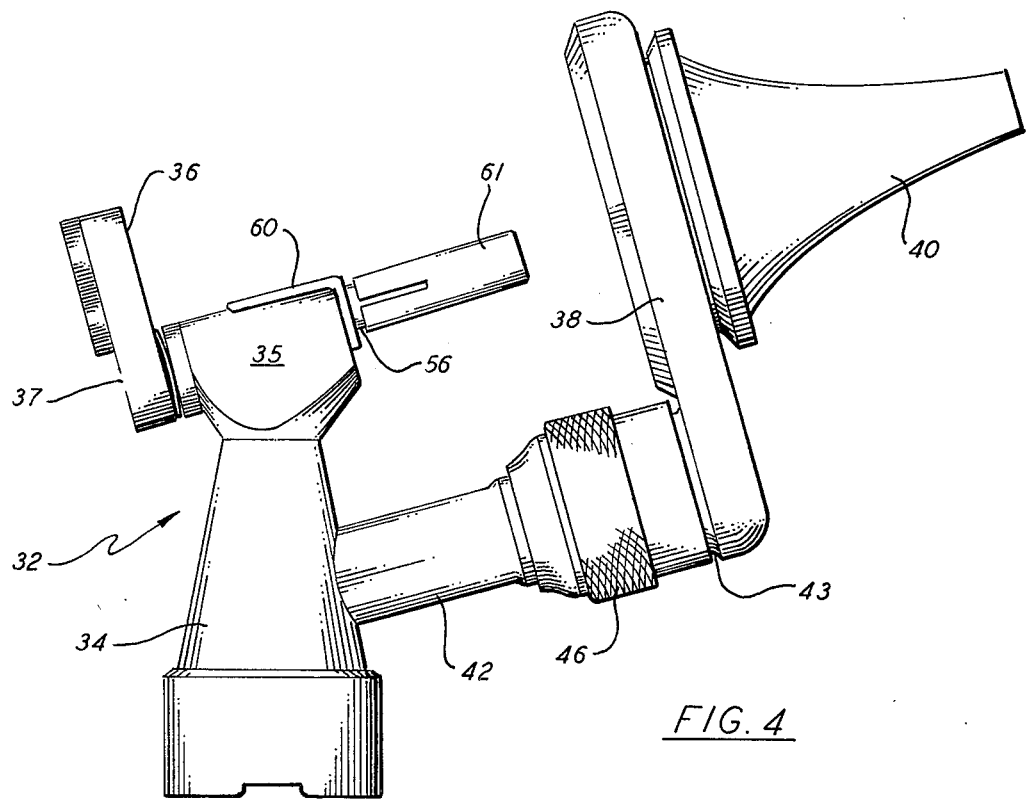
FIG. 4 is a side elevation of an operating type otoscope embodying the invention.

Referring now to the drawings, and with particular reference to FIGS. 1–3, there is shown a diagnostic type otoscope 10 mounted on a battery handle 11 such as is disclosed in U.S. Pat. No. 3,071,747, issued Jan. 1, 1963 to W. C. Moore, one of the applicants herein. The battery handle is held by the physician in using the instrument, and contains batteries (not shown), a switch button 12 and a rheostat dial 14. The batteries supply power to a lamp to be described.

Otoscope 10 is comprised of an upper, substantially cylindrical portion 15 having a viewing passage 16, FIG. 3, therethrough and a base or neck portion 17 the lower end of which is removably connected to the battery handle. A conventional ear speculum 18 is releasably secured to the front side of the otoscope, the speculum shown being interchangeable with ear and nasal specula of various sizes. At the rear of the otoscope there is a closure in the form of a lens frame 20 and lens (not shown). The frame is pivotally connected in a conventional manner to the otoscope at 21 whereby it can be swung upwardly to open the rear of the instrument.

A diagnostic otoscope, also sometimes called a closed head otoscope, can be used to introduce air into the ear canal so that the physician can observe its effect on the tympanic membrane. To this end, the otoscope is provided with a fitting 22 for a pneumatic attachment (not shown).

In accord with the invention, the base portion 17 of the otoscope is formed with a recess 24, FIG. 2, that is dimensioned to receive with a close fit a larger than normal lamp 25 which is preferably a halogen lamp. The lamp is connected in a conventional manner to the batteries in the battery handle whereby it can be turned on and off by the switch 12. The light from lamp 25 is transmitted to a point in the viewing passage 16 by a bundle of clad optical fibers 26 that are encased in a metal tube 27. At the ends of the tube, the fibers are optically ground and polished, and the tube is bent as shown so the light rays are emitted from its upper end in a direction that is substantially parallel to the centerline of the otoscope viewing passage and speculum.

The lower end of the fiber optic tube 27 is received with a sliding fit in a second tube 28 that is mounted with a press fit in the recess 24 and extends from a point adjacent the top of the lamp to a terminus just inside the portion 15 of the otoscope. The tube 27 is held in tube 28 by a set screw 30. With this arrangement if there is any damage to the fibers, it is only necessary to replace the tube and fiber assembly and not the entire instrument. The bottom of the lamp recess is open permitting easy insertion and withdrawal of the lamp.

Because lamp 25 is larger than normal, it provides more light at the field of view adjacent the distale end of speculum 18. If this larger lamp were placed in the conventional location in the viewing passage it would, of course, be more of an obstruction. The fiber optic tube 17, on the other hand, occupies less space than a normal lamp and its mounting, and therefore is less of an obstruction. The fiber optic bundle has the further advantage of making the illumination more uniform and of eliminating altogether the filament image that appears in the illuminated field when either a vacuum or a halogen lamp is in the usual location.

In addition to giving more light, the halogen lamp 25 gives a whiter light which is desirable. However, because it is larger, the lamp generates more heat and could cause injury if touched. By locating the lamp in the recess 24 the surrounding metal acts as a heat sink and absorbs and dissipates the heat so that the instrument does not get too hot. This location also removes the lamp from an exposed position so that it is protected from dirt, oils and other foreign matter. In the case of a halogen lamp, the location insures proper elevated lamp operating temperature.

Figure 5:
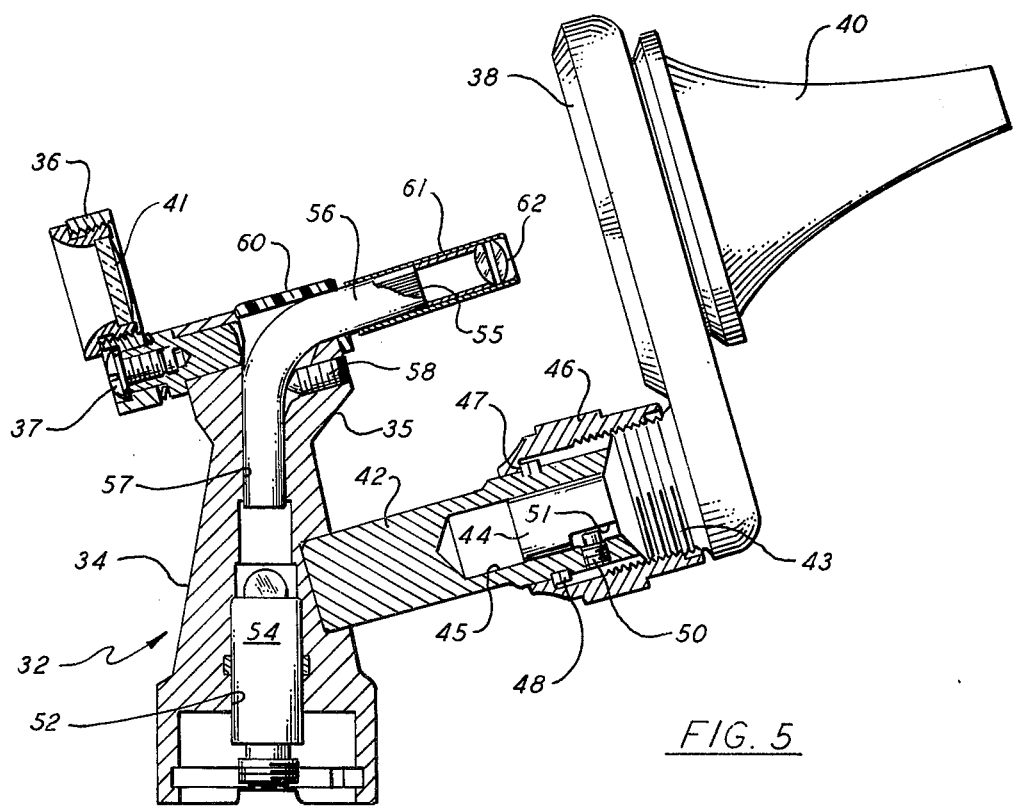
FIG. 5 is a view corresponding to FIG. 4 with a portion of the otoscope being shown in section.

Referring now to FIGS. 4 and 5, there is shown an operating or open head type otoscope 32 embodying the invention. Otoscope 32 includes a base or neck portion 34 and an upper portion comprised of a head portion 35, a lens frame 36 pivotally connected to the head portion at 37 and a speculum holder 38 in which a speculum 40 is releasably secured. The viewing passage through this otoscope is on a line extending from the approximate center of the lens frame 36 to the approximate center of the distal end of speculum 40.

The base portion 34 of the otoscope is adapted to be removably connected to a battery handle as shown in FIG. 1 and receive from it current for its lamp, to be described. The lens frame 36 carries a magnifying lens 41, FIG. 5; the lens and frame can if desired by swung downwardly out of the viewing passage because of the pivotal connection 37.

Projecting forwardly from the base portion 34 is an arm 42 to which the speculum holder 38 is connected for limited rotational movement. To this end, the holder has a threaded boss 43 from which a stub shaft 44 of reduced diameter projects. The shaft is received with a sliding fit in a bore 45 in the outer end of the arm 42.

A lock nut 46 on the arm 42 is threaded onto the boss 43, the back end of the nut having an interior annular shoulder 47 that abuts against a pair of lock rings 48 mounted in an annular groove in the arm. The two lock rings permit rotational movement of the speculum holder relative to the arm 42 even though the lock nut is tightened on the boss 43. Rotational movement of the speculum holder is limited by a set screw 50 that projects into a slot 51 in the stub shaft 44, the angular extent of the slot being about 30°.

Like the diagnostic otoscope 10 in FIG. 1–3, the base portion 34 of otoscope 32 is formed with a recess 52 that is dimensioned to receive a larger than normal lamp 54, preferably a halogen lamp. Light is transmitted from the lamp to a point in the viewing passage by a bundle of optical fibers 55 encased in a metal tube 56. The tube and fiber assembly is substantially the same as the corresponding assembly 26,27 in otoscope 10, the tube being bent as shown so that the light rays are emitted in a direction parallel to the axis of speculum 40.

The lower end of the fiber optic tube 56 is received with a sliding fit in an upper, reduced diameter portion 57 of the lamp recess 52, and is held in the position shown by a set screw 58. This, as noted above, permits easy replacement of the tube and fiber assembly should that become necessary. At its top, the recess portion 57 is open or saddle shaped so that the fiber optic tube 56 can simply be dropped into position and the set screw tightened. Above the tube, the opening is occupied by a plastic cover member 60 that is received in the opening with a press fit.

At its upper end, the fiber optic tube 56 is telescopically engaged by a lens cap assembly comprising a tube 61 having a double convex lens 62 at its outer end as shown in FIG. 5. The purpose of this assembly is to reduce the angle of the cone of light leaving the fiber optic tube and thus insure that substantially all of this light will pass through the opening at the distal end of the speculum 40.

As in the diagnostic otoscope 10, the utilization of a larger than normal lamp provides more light at the field of view but by locating the lamp in the base portion of the otoscope there is less rather than more of an obstruction in the viewing passage. The other advantages derived from using a halogen lamp and a fiber optic light transmitting bundle, as described above, are also present in the operating type otoscope just described.

From the foregoing description, it will be apparent that the invention provides a greatly improved and very advantageous otoscope construction. As will be understood by those familiar with the art, the invention may be embodied in other specific forms without departing from the spirit or essential characteristics thereof.

We claim:

1. A high light output otoscope comprising an upper portion having a viewing passage therethrough and a base portion adapted to be releasably connected to a battery handle, the upper portion including a removable speculum, a recess in the base portion for receiving a larger than normal otoscope lamp, and a bundle of optical fibers mounted in the otoscope, the bundle having a light receiving end positioned adjacent the lamp and a light emitting end positioned so as to direct light received from the lamp in a path substantially parallel to the viewing passage, the light emitting end of the bundle terminating at a point adjacent the proximal end of the removable speculum and being located close to the projected center line of the speculum.

2. An otoscope as defined in claim 1 together with a halogen lamp positioned in the recess.

3. An otoscope as defined in claim 2 wherein the base portion of the otoscope operates as a heat sink for the lamp.

4. An otoscope as defined in claim 1 that is a diagnostic type otoscope.

5. An otoscope as defined in claim 1 that is an operating type otoscope.

6. An otoscope having a high output of uniform, white light; the otoscope comprising an upper portion with a viewing passage therethrough and a base portion adapted to be releasably connected to a battery handle, the upper portion including a removable speculum, the base portion having a central recess therein, a halogen lamp received with a close fit in the recess and arranged to draw current from the battery handle, and a bent light pipe assembly mounted in the otoscope for transmitting light from the lamp to a point in the upper portion of the otoscope, the light pipe assembly comprising a tubular casing occupied by a bundle of optical fibers, the assembly having a light receiving end positioned adjacent the lamp and a light emitting end positioned so as to direct light received from the lamp in a path substantially parallel to the viewing passage, the light emitting end of the assembly being laterally offset from but close to the centerline of the viewing passage, the light emitting end of the bundle terminating at a point adjacent the proximal end of the removable speculum.

7. An otoscope as defined in claim 6 that is a diagnostic type otoscope.

8. An otoscope as defined in claim 6 that is an operating type otoscope.

9. An otoscope as defined in claim 8 together with a lens cap assembly mounted on the light emitting end of the light pipe assembly, the lens cap assembly comprising a tube forming an extension of the light pipe assembly and a lens positioned in the outer end of the tube.

* * * * *